United States Patent [19]
Visscher et al.

[11] Patent Number: 5,261,899
[45] Date of Patent: Nov. 16, 1993

[54] MULTILAYER FILM EXHIBITING AN OPAQUE APPEARANCE

[75] Inventors: Ronald B. Visscher; Bruce F. Perry, both of Cincinnati, Ohio

[73] Assignee: The Procter & Gamble Company, Cincinnati, Ohio

[21] Appl. No.: 863,936

[22] Filed: Apr. 6, 1992

[51] Int. Cl.$^5$ ............................................. A61F 13/15
[52] U.S. Cl. ..................................... 604/367; 604/358
[58] Field of Search ............... 604/367, 358, 383, 384; 428/131, 138; 602/41, 52

[56] References Cited

U.S. PATENT DOCUMENTS

| | | | |
|---|---|---|---|
| 3,929,135 | 12/1975 | Thompson | 128/287 |
| 3,952,745 | 4/1976 | Duncan | 128/287 |
| 4,151,240 | 4/1979 | Lucas et al. | 264/504 |
| 4,342,314 | 8/1982 | Radel et al. | 128/287 |
| 4,463,045 | 7/1984 | Ahr et al. | 428/131 |
| 4,552,709 | 11/1985 | Koger, II et al. | 264/504 |
| 4,690,679 | 9/1987 | Mattingly, III et al. | 604/383 |
| 4,710,186 | 12/1987 | DeRossett et al. | 604/383 |
| 4,806,411 | 2/1989 | Mattingly, III et al. | 428/139 |
| 5,006,394 | 4/1991 | Baird | 428/138 |

FOREIGN PATENT DOCUMENTS 0304617 3/1989 European Pat. Off. .

OTHER PUBLICATIONS

Copending Application Ser. No. 07/817,016 filed Jan. 3, 1992, Goodman et al., entitled "Resilient Plastic Web Exhibiting Reduced Skin Contact Area and Enhanced Fluid Transfer Properties".

Primary Examiner—David Isabella
Assistant Examiner—Gina M. Gualtieri
Attorney, Agent, or Firm—Kevin C. Johnson; E. Kelly Linman

[57] ABSTRACT

A polymeric multilayer film having a high percentage of fillers to increase the opacity of the film is disclosed. The fillers are concentrated in a separate filler containing layer having about 20 to about 60 weight percent fillers uniformly dispersed therein and about 30 to about 70 percent of the thickness of the total multilayer film. The filler containing layer is coextruded with the outer layers comprising the balance of the thickness of the multilayer film. The multilayer film has at least 15 weight percent fillers.

18 Claims, 3 Drawing Sheets

MULTILAYER FILM EXHIBITING AN OPAQUE APPEARANCE

FIELD OF THE INVENTION

This invention relates to polymeric multilayer films having one or more fillers, and more particularly, to such multilayer films having high concentrations of fillers to increase the opacity of the film.

BACKGROUND OF THE INVENTION

It has long been known in the disposable absorbent bandage art that it is extremely desirable to construct absorptive devices, such as sanitary napkins, disposable diapers, incontinent articles, and the like, presenting a dry surface feel to the user to improve wearing comfort and to minimize the development of undesirable skin conditions due to prolonged exposure to moisture absorbed within the bandage.

One viable prior art solution to the aforementioned problem is disclosed in commonly assigned U.S. Pat. No. 4,342,314 issued to Radel et al. on Aug. 3, 1982 and hereby incorporated herein by reference. Radel et al. discloses an absorbent bandage with a wearer-contacting topsheet comprising a resilient macroscopically expanded, three-dimensional plastic web exhibiting a combination of fiber-like and plastic properties. In a preferred embodiment, the macroscopically expanded three-dimensional plastic web topsheet disclosed in Radel et al. exhibits a fine scale three-dimensional microstructure comprising a regulated continuum of capillary networks, of steadily decreasing size, originating in and extending from one surface of the web and terminating in the form of apertures in the opposite surface thereof to promote rapid fluid transport in the direction of decreasing capillary size. The web's fiber-like appearance is comprised of a continuum of fiber-like elements, the opposed ends of each of the fiber-like elements being interconnected to at least one other of the fiber-like elements.

To reduce the gloss of the Plastic web's visible surface, i.e., that portion of the web which is visible from directly overhead, it has been learned that inclusion of a microscopic pattern of surface aberrations which are not discernible when the perpendicular distance between the viewer's eye and the plane of the web is about 12 inches is highly effective. Commonly assigned U.S. Pat. No. 4,463,045 issued to Ahr et al . on Jul. 31, 1984 and hereby incorporated herein by reference defines the relevant criteria which must be satisfied so that the three-dimensional expanded web will exhibit a substantially non-glossy visible surface.

A topsheet of the type generally disclosed by Radel et al., having surface aberrations according to Ahr et al., exhibits a fiber-like appearance and tactile impression as well as a non-glossy visible surface. In addition, it is highly effective in promoting rapid fluid transfer from the first wearer-contacting surface to the second pad contacting surface of the topsheet. Topsheets of the latter type have enjoyed wide spread commercial success on catamenial pads due to their highly effective fluid transfer and their clean and dry appearance in use when contrasted to conventional nonwoven fibrous topsheets.

However, the effective fluid transfer and storage of bodily fluids by such structures has allowed for long wearing times and significant fluid absorption prior to disposal. These concentrations of bodily fluids, particularly menses, in the absorbent core tend to be somewhat visible through the opaque topsheet.

Accordingly, it is an object of the present invention to provide a thin opaque multilayer film which can be processed into a formed-film, and which contains a high concentration of pigments or other fillers to increase the masking ability of the formed-films.

It is also an object of the present invention to provide a multilayer film which can be processed into a formed-film, and which contains a high concentration of pigments or other fillers located in a separate filler layer which is relatively thick, thereby providing a formed-film having an increased opacity, but which is nonetheless readily machinable, i.e., it can be produced at a relatively high speed, e.g., at commercial speeds on the order of several hundred feet per minute.

SUMMARY OF THE INVENTION

The present invention provides a polymeric multilayer film which exhibits an opaque appearance. The multilayer film comprises a first outer layer comprised substantially of a polymeric material and a central filler containing polymeric layer substantially continuously joined to one side of the first outer layer. The filler containing layer has from about 20 to about 60 weight percent fillers relative to the filler containing layer which are substantially uniformly dispersed therein and a thickness from about 25 to about 80 percent of the total thickness of the multilayer film. A second outer layer comprised substantially of a polymeric material has one side substantially continuously joined to the second side of the central filler containing layer. The multilayer film contains at least 15 weight percent opacifying fillers relative to the total multilayer film, such that the fillers in the central filler containing layer scatter light rays incident upon the multilayer film to produce an opaque appearance in the multilayer film.

In a preferred embodiment the multilayer film is processed into a formed-film having a multiplicity of apertures therein. More preferably, the formed-film is used as a topsheet on an absorbent bandage.

BRIEF DESCRIPTION OF THE DRAWINGS

While the specification concludes with claims particularly pointing out and distinctly claiming the subject matter of the present invention, it is believed that the present invention will be better understood from the following description taken in conjunction with the accompanying drawings in which like reference numerals identify identical elements and wherein;

DETAILED DESCRIPTION OF THE INVENTION

Figure 1:
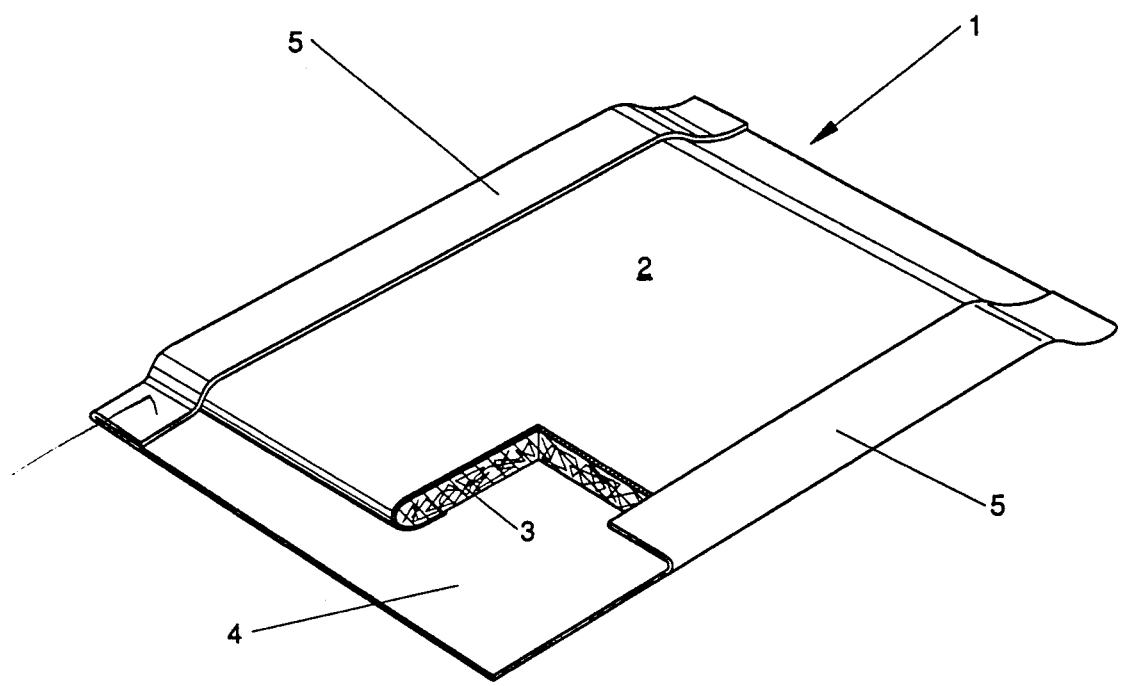
FIG. 1 is a simplified perspective representation of an unfolded disposable diaper with portions of its components cut away.

FIG. 1 is a perspective view of a disposable diaper in an unfolded condition. Various layers have been cut away to more clearly show the structural details of this embodiment. The disposable diaper is referred to generally by the reference numeral 1. The fluid-pervious topsheet is shown at 2. The other two major components of the disposable diaper 1 are the absorbent element or pad 3 and the fluid-impervious backsheet 4. In general, the side flaps 5 of the backsheet 4 are folded so as to cover the edges of the absorbent pad 3 and topsheet 2. Topsheet 2 is generally folded to completely enclose the ends of the absorbent pad 3. The drawing of diaper 1 in FIG. 1 is a simplified representation of a disposable diaper. A more detailed description of a preferred embodiment of a disposable diaper is contained in commonly assigned U.S. Pat. No. 3,952,745 issued to Duncan on Apr. 27, 1976, said patent being hereby incorporated herein by reference.

Figure 2:
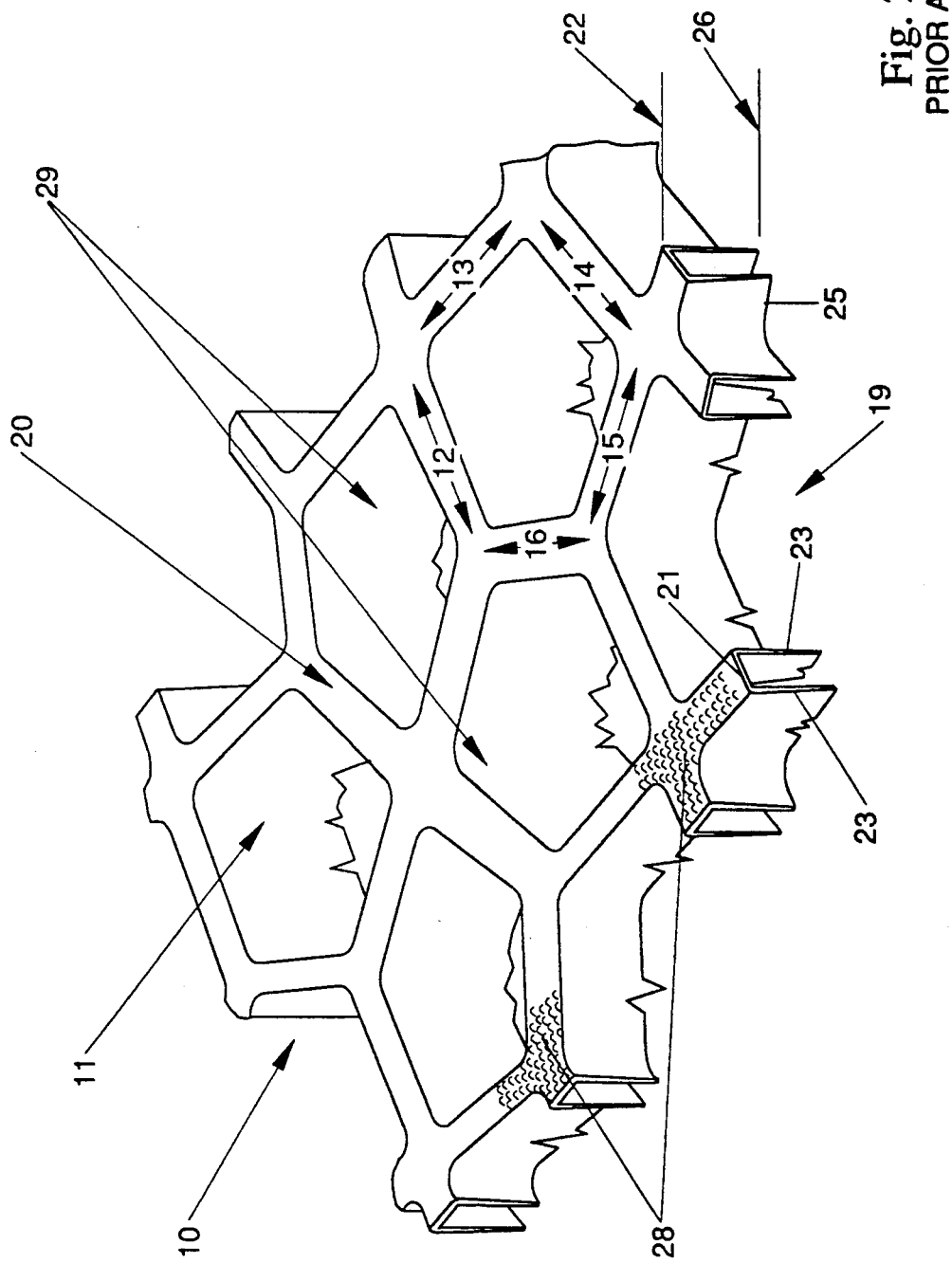
FIG. 2 is an enlarged, partially segmented, perspective illustration of a prior art plastic web of a type generally disclosed in commonly assigned U.S. Pat. No. 4,342,314, said web further exhibiting a microscopic pattern of surface aberrations of the type generally disclosed in commonly assigned U.S. Pat. No. 4,463,045 on its visible surface.

FIG. 2 is an enlarged, partially segmented, perspective illustration of a prior art three-dimensional, fiber-like, fluid pervious plastic web 10 which has been found highly suitable for use as a topsheet in disposable absorbent bandage structures, such as sanitary napkins. It may, if desired, also be employed as a topsheet 2 in disposable diaper 1 shown in FIG. 1. The prior art web 10 is generally in accordance with the teachings of commonly assigned U.S. Pat. No. 4,342,314 issued to Radel et al. on Aug. 3, 1982, which is incorporated herein by reference. Fluid permeable topsheets prepared in the manner of the Radel et al. patent are conveniently referred to as "formed-films". The fluid pervious web 10 illustrated in FIG. 2 exhibits a multiplicity of apertures, e.g., apertures 11, which are formed by a multiplicity of intersecting fiber-like elements, e.g., elements 12, 13, 14, 15, and 16, interconnected to one another in the first surface 20 of the web. Each fiber-like element comprises a base portion, e.g., base portion 21, located in plane 22. Each base portion has a sidewall portion, e.g., sidewall portion 23, attached to each edge thereof. The sidewall portions extend generally in the direction of the second surface 25 of the web. The intersecting sidewall portions of the fiber-like elements are interconnected to one another intermediate the first and second surfaces of the web, and terminate substantially concurrently with one another in the plane 26 of the second surface.

In a preferred embodiment, the base portion 21 includes a microscopic pattern of surface aberrations 28, generally in accordance with the teachings of commonly assigned U.S. Pat. No. 4,463,045 issued to Ahr et al. on August 31, 1984 and incorporated herein by reference. The microscopic pattern of surface aberrations 28 provide a substantially non-glossy visible surface when the web is struck by incident light rays.

In a preferred embodiment, the interconnected sidewall portions terminate substantially concurrently with one another in the plane of the second surface to form apertures 19 in the second surface 25 of the web. The capillary network 29 formed by the interconnected sidewall portions allows for free transfer of fluids from the first surface of the web directly to the second surface of the web without lateral transmission of the fluid between adjacent capillary networks.

Other types of formed-film topsheets that can be used herein are disclosed in commonly assigned U.S. Pat. No. 3,929,135 issued to Thompson on Dec. 30, 1975, which is hereby incorporated herein by reference, and commonly assigned copending U.S. patent application entitled "RESILIENT PLASTIC WEB EXHIBITING REDUCED SKIN CONTACT AREA AND ENHANCED FLUID TRANSFER PROPERTIES" Ser. No. 07/817,016 filed Jan. 3, 1992, Inventors, Goodman and Gerth, the specification of which is also hereby incorporated herein by reference.

Alternatively, the present invention may be practiced in the context of a topsheet exhibiting a two-dimensional structure. A two-dimensional topsheet is a substantially planar structure having apertures therein.

As noted earlier herein, the more effective fluid transfer and storage of bodily fluids by prior art formed-film topsheets used on disposable absorbent bandages, such as catamenial pads, has allowed for long wearing times and significant fluid absorption prior to disposal. These greater concentrations of bodily fluids, particularly menses, in the absorbent core tend to be somewhat visible through the opaque topsheet. Formed-film topsheets of the present invention exhibit sufficient capacity to partially mask the bodily fluids in the absorbent core so as not to detract from the normally clean and dry appearance provided by the formed-film topsheet.

Figure 3:
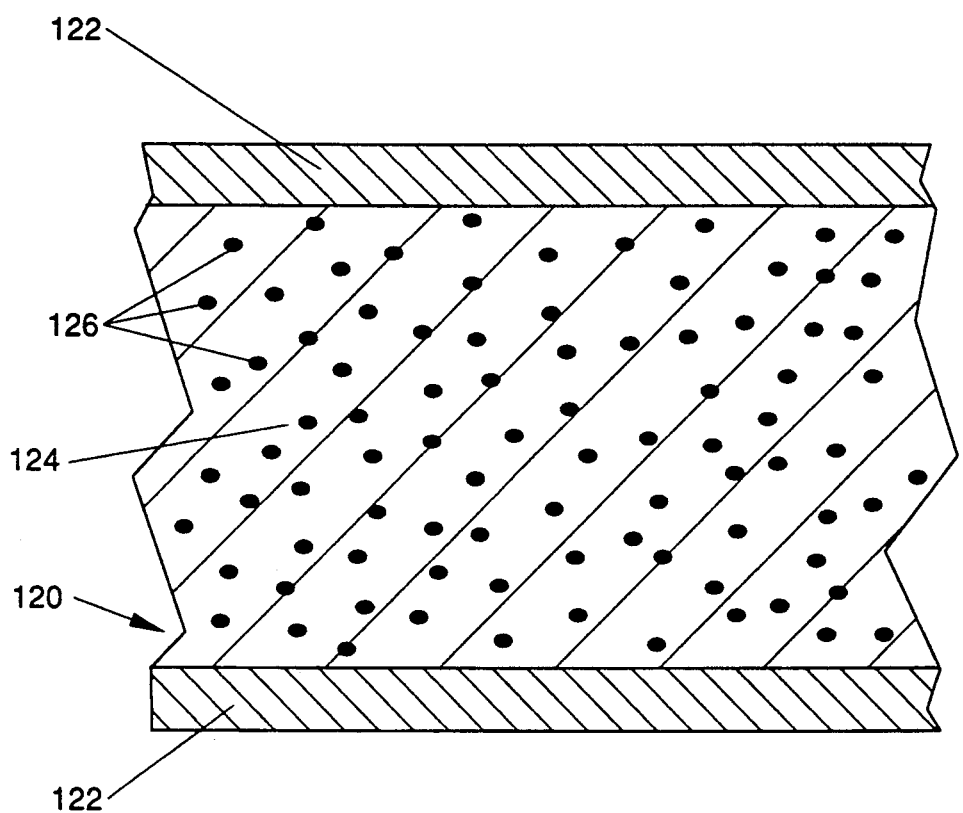
FIG. 3 is a cross-sectional view of the multilayer film of the present invention having one central filler containing layer between two outer layers.

FIG. 3 is a cross-sectional view of a polymeric, multilayer film 120 which can be used in making formed-film topsheets of the present invention. The multilayer film has at least three layers and a total thickness of about 0.25 mm (0.01 inches) or less. The two outer layers 122, are made of conventional polymeric materials, e.g., polethylene. Interposed between the two outer layers 122 is a central filler containing layer 124, having opposed first and second sides, each side is substantially continuously joined to one side of one of the outer layers 122. The third central layer 124 comprises from about 25 percent to about 80 percent of the total film thickness and contains a high percentage of opacifying fillers 126. The two outer layers 122 comprise the balance of the film 120.

Preferably the outer layers 122 comprise from about 20 percent to about 75 percent of the total thickness of multilayer film 120, more preferably from about 30 percent to about 70 percent of the total thickness of the multilayer film 120, and most preferably from about 40 percent to about 60 percent of the total thickness of the multilayer film 120. By maintaining the outer layers 122 to a thickness totaling no more than 75 percent of the multilayer film 120, the opacity of the multilayer film 120 approximates that of the central filler layer 124, and is not significantly affected by the lack of opaque filler in the outer layers 122.

The material selected for the outer layers 122 must be machinable and capable of being formed into a film. Particular attention should be given to properties after finishing into an formed-film including tear resistance, tensile strength, elastic modulus and any other properties required by the application. Since the film 120, in a particularly preferred embodiment, is to be formed into a formed-film for use in consumer products which contact the human body, the film 120 must also be soft and safe for epidermal or other human contact. Preferred polymeric materials for outer layers 122 include polyolefins, particularly polyethylenes, polypropylenes and copolymers having at least one olefinic constituent. Other materials such as polyesters, nylons, copolymers thereof and combinations of any of the foregoing may also be suitable.

If desired, conventional amounts of whiteners (not shown), typically 1 to 15 weight percent, based on the outer layers 122, may be added to the polymeric matrix of the outer layers 122 to increase their opacity. The percentage of whiteners, such as titanium dioxide and calcium carbonate, are limited by the material properties of the outer layers 122, and the application to which the film 120 is to be applied. For example, if the multilayer film 120 of the present invention is employed in a diaper or catamenial pad, the outer layers 122 having filler levels above approximately 10 weight percent, based on outer layers 122, may result in a multilayer film 120 which is unpleasant and harsh feeling when placed against the skin.

The central layer 124, or polymeric filler containing layer, comprises a polymeric matrix and high concentrations of pigments or other machinable fillers 126. Materials suitable for the central polymeric matrix include polyolefins, such as polyethylenes and polypropylenes, and copolymers having at least one olefinic constituent. Other materials such as polyesters, and nylons, copolymers thereof, and combinations of any of the foregoing may be suitable. Because a flexible and elastic matrix is desirable to accommodate the high concentrations of fillers 126, a relatively softer material such as linear low density polyethylene polymer works well.

To cause opacification, whitening or coloring of central layer 124, approximately 20 to approximately 60 weight percent pigment fillers 126 may be added. Since a film 120 having a whitish appearance, in addition to being opaque, is often desirable, particularly if such film 120 is to be used in disposable consumer products such as catamenial pads, diapers, etc., a whitening pigment such as titanium dioxide or calcium carbonate may be selected. Other useful fillers 126 include colored pigments such as carbon black, etc. To reinforce the multilayer film 120, filament fillers, such as rayon, may be added to the central layer 124.

By utilizing light refracting fillers 126, which have a refractive index different than that of the polymeric matrix of central layer 124, a white opaque film 120 can be produced without stretching of the film 120 as part of the manufacturing process. The pigmentation of central layer 124 results from the scattering of light rays refracted from fillers 126, and not as a result of voids created by stretching of film 120. Titanium dioxide, calcium carbonate and silica work well with the polymers described above to cause whitening and opacification by light refraction.

The central layer 124 preferably comprises from about 25 to about 80 percent of the total thickness of multilayer film 120, and more preferably comprises from about 30 to about 70 percent of the total thickness of multilayer film 120, and most preferably comprises from about 40 to about 60 percent of the total thickness of multilayer film 120. This proportion of layers is important to prevent the central layer 124 from causing the multilayer film 120 to have an excessively brittle or tearable nature. Also, if the multilayer film 120 is to be placed in contact with the skin, more comfort is provided if the central layer 124 is joined to more compliant outer layers 122. Even though the central layer 124 comprises relatively high percentages of the total thickness of multilayer film 120, the desirable material properties of the multilayer film 120 are substantially maintained.

It is important that the multilayer film 120 have sufficient fillers to provide the desired opacity. Preferably, the multilayer film 120 has greater than about 15 weight percent fillers based on the total thickness of film 120, preferably titanium dioxide, to provide the desired opacification. As the thickness of the central layer 124 is increased, the weight percent of fillers in the central layer can be decreased, and still provide a film 120 having at least 15 weight percent fillers based on the total thickness of film 120. An example of a multilayer film 120 having greater than about 15 weight percent titanium dioxide has a central layer 124 comprising 60 percent of the total thickness of multilayer film 120 and containing 25 weight percent titanium dioxide. Another example is a multilayer film 120 having a central layer 124 comprising 40 percent of the total thickness of multilayer film 120 and containing 38 weight percent titanium dioxide. More preferably, the multilayer film 120 has greater than about 20 weight percent titanium dioxide. An example of such a multilayer film 120 has a central layer 124 comprising 40 percent of the total thickness of the multilayer film 120 and containing 50 weight percent titanium dioxide. Another example is a multilayer film 120 having a central layer 124 comprising 50 percent of the total thickness of the multilayer film 120 and containing 40 weight percent titanium dioxide.

It is necessary that the thickness of the central layer 124 be coordinated with the particle size and percentages of any fillers 126 added to central layer 124. Fillers 126 having an average particle size of about 0.5 to 8 microns are typically suitable. As the thickness of the central layer 124 is increased, the weight percent of fillers in the central layer 124 is decreased to provide the desired opacity for multilayer film 120. For example, if a relatively thin central layer 124 is selected, the weight percent of filler will accordingly be relatively high. A structure of this type will have a relatively brittle central layer. However, because the outer layers 122 will be relatively thick, the multilayer film 120 can be processed into a formed-film for use as a topsheet on a catamenial appliance. By comparison if a relatively thick central layer 124 is selected, the weight percent of filler can be reduced when compared to a relatively thin central layer. A structure of this type will have relatively thin outer layers 122. However, because the central layer 124 can contain a relatively low percentage of fillers, the multilayer film 120 can be processed into a formed-film for use as a topsheet on a catamenial appliance.

The thickness of central layer 124 also constrains the weight percentage of fillers which may be added to the central layer 124. While filler concentrations exceeding 60 weight percent are possible with the multilayer film 120 of the present invention, the filler concentrations must be low enough to allow the particles 126 to be fully dispersed throughout the polymeric matrix of the central layer 124, and not stacked in a solid, relatively continuous fashion from the interface with the outer layers 122 to the outer surface of central layer 124.

Filler concentrations of less than 15 weight percent are also feasible, but generally do not require the multilayer film 120 of this invention. Films having filler concentrations of less than 15 weight percent typically can be achieved by methods known in the prior art. However, disadvantages of filler concentrations of greater than 15 percent, such as a harsh tactile sensation of the outer surfaces of said film, can be overcome by providing the film of the present invention having outer layers 122 of very low filler concentration which are placed against the skin and a central filler containing layer 124 which is shielded from the skin by the outer layers 122.

The layers described above, must be joined, preferentially continuously, to yield a unitary multilayer film 120. A preferred method to produce the multilayer film 120 is coextrusion.

It is important that the polymers selected for the central and outer layers be compatible and self adhering to the each other, to prevent problems in joining the three layers into a substantially continuous unitary multilayer film 120. If the layers are joined by coextrusion, it is furthermore important that the polymers of the three layers have somewhat closely matched melt indicies and melting points.

If the layers are not compatible and self adhering, a tie layer or compatibilizing layer (not shown) can be interposed between the outer layers 122 and the central layer 124. The compatibilizing or tie layer typically is a copolymer of the layers between which such layer is interposed and has properties intermediate those layers adjoining it.

To coextrude a multilayer film 120 of the present invention, having three layers, polymer resin pellets of the outer layers 122 and 0 to 15 weight percent pigment, or other fillers are provided and mixed in a hopper until a substantially homogeneous first mixture is obtained. To form the composition of central layer 124, polymer resin containing pellets of the central layer 124 and approximately 15 to approximately 60 weight percent filler 126 are provided. The filler 126 containing pellets may comprise one or more types of fillers 126, including pigments, when mixed with the polymer resin pellets of the central layer 124. The filler 126 containing pellets and central layer 124 polymer resin pellets are then mixed in a hopper until the filler and polymer resin pellets are substantially evenly dispersed in a substantially homogeneous second mixture.

The two homogeneous mixtures are preferably fed into separate plasticating extruders coupled to a coextrusion feed block adapted to yield the desired proportion, typically approximately 4:6 of the first and second outer layers 122 to the central filler containing layer 124. The mixtures are melted in the plasticating extruders and then simultaneously extruded through the coextrusion feed block under the conditions of pressure and temperature which are proper for the selected pellets, yielding a substantially continuous coextruded multilayer sheet having a cross section of the desired proportion of outer layers 122 to central layer 124.

The substantially continuous multilayer sheet emerging from the coextrusion feed block is then fed into a coat hanger type film die of the type well known in the art, or other film die of rectangular cross section and adapted to maintain laminar flow, to yield a substantially continuous coextruded multilayer film having a thickness of less than about 0.5 mm (0.02 inches). The proportions of the layers are not changed as the multilayer film is extruded through the die and will remain in the selected proportion, say 4:6.

The substantially continuous multilayer film is then fed onto a rotating chill roll which causes freezing, or crystallization, of the multilayer film. The rotating chill roll should have a surface velocity equal to, or preferably greater than that of the multilayer film as it emerges from the film die, so that no accumulation of the film occurs. This difference in relative surface velocities also results in additional thinning, or necking, of the sheet to a film of the desired finished thickness, typically less than about 0.25 mm (0.01 inches). The film, after leaving the chill roll, is then rolled or otherwise stored as convenient. Alternatively, the multilayer film can be fed directly into a secondary converting process.

An alternative to the coextrusion feed block and film die system, discussed above, is to utilize a coextrusion die in place of the coextrusion feed block and film die system. A coextrusion die receives the substantially homogeneous mixtures from the plasticating extruders, and coextrudes a multilayer film of the desired proportions, as described above, which is then fed onto the rotating chill roll.

A second process to produce the multilayer film of this invention is a coextruded blown film process. Two substantially homogenous mixtures are provided as described above and fed into plasticating extruders coupled to a coextrusion blown film die of circular cross section and having an annular orifice adapted to yield a proportion of outer layers 122 to central layer 124 ranging of typically approximately 4:6. The two homogeneous mixtures are melted in the plasticating extruders and emerge from the lips of the die in a continuous vertical sheet, having the shape of a tapered hollow cylinder, which is drawn away from film die by pull rolls.

Gas or air is simultaneously fed through the film die, at a location internal the hollow cylinder, and into the continuous multilayer sheet, causing it to radially expand. As the continuous multilayer sheet rises it is cooled and frozen by heat transfer to the surrounding air. After solidifying, the multilayer sheet is collapsed and folded or rolled, then stored as desired.

The film according to either process above is then formed by drawing such film against a forming screen by means of a vacuum and passing an air or water jet over the outwardly posited surface of the film. Such processes are described in commonly assigned U.S. Pat. Nos. 4,342,314 issued to Radel et al . on Aug. 3, 1982, and 4,154,240 issued to Lucas et al., both being incorporated herein by reference. Alternatively, the film can be formed prior to being fed onto the chill roll, as described in U.S. Pat. No. 4,552,709 issued to Koger, II et al., incorporated herein by reference.

While the foregoing examples of the coextrusion process are directed to a three layer multilayer film 120 where the outer layers are identical in composition, it will be apparent to one skilled in the art that by adding a third homogeneous mixture, and adjusting the coextrusion feed block or film die of the plasticating extruder to produce a layered structure of the desired proportions, a three layer multilayer film is possible where all three layers are unique. This arrangement provides the advantage that either surface of multilayer film 120 can be made soft, compliant, and tactually pleasant to the skin, through the selection of materials, such as alpha-olefin polymers, for outer layers 122. Also, the outer layers 122 may contain different colored pigments. If a first colored pigmentation is employed in one of the outer layers 122, and white or a second colored pigmentation in the remaining layer of the outer layers 122, it is possible to produce a thin film 120 with each side having a different color.

It will be apparent that modified three layer structures having two juxtaposed outer layers and a central filler containing layer may easily be constructed. Furthermore, four or more layer structures are possible and the structures described above may be combined to give structures having multiple layers. However, the material properties, opacity, and processing of such multiple layer structures essentially conforms to that described above.

Having preferably been formed into a structure as disclosed in FIG. 2, the multilayer formed-film shall have sufficient opacity to mask bodily fluids, specifically menses, which have been transmitted therethrough. The opacity of the formed-film is defined as the square of the ratio of the amount of light reflected from a material when it is backed by a black standard surface over the amount of light reflected from the same material when it is backed by a standard white surface. This ratio is expressed as a percentage. The reflectance is measured using the Hunter L value, well known in the field of colorimetry. A complete definition of the Hunter L value can be found in Principles of Color Technology, 2nd ed. Billmeyer & Salzman, Wiley, 1981, incorporated herein by reference.

There exits a variety of photoelectric reflectance photometers which can perform the Hunter L measurement. A particularly suitable instrument is the Elrepho 2000, manufactured by ACS Datacolor of Westchester, Ill. This instrument and its calibration and operation are described in the Mar. 5, 1990 revision of the operating instructions for the Elrepho 2000, published by ACS Datacolor, order number 700 373, and incorporated herein by reference. The basic operation for measuring the opacity using Hunter L measurements can be summarized as follows. The machine is set up using its 18-mm orifice and calibration proceeds according to the operating instruction using black and white standards. For the Elrepho 2000, the black standard is a minimally reflecting black box, and the white standard is a highly reflective white ceramic chip MC-20. The opacity measurement is made by first placing a sample of the formed-film on top of the black standard such that the body-facing surface of the formed-film faces away from the standard. Then the combination of black standard and formed-film samples are inserted into the light path of the Elrepho 2000 such that the formed-film sample faces the instrument's light source, with the black standard backing it. The sample is exposed to light and the Hunter L value is measured. This process is repeated using the white standard in place of the black standard. The ratio of the Hunter L value for the formed-film sample backed by the black standard over the Hunter L value for the formed-film sample backed by the white standard is calculated. This ratio is then squared to provide the value of opacity.

The homogeneous prior art formed-film as currently being marketed on catamenial pads and having a filler content of 4 weight percent fillers exhibits an opacity of 35.3 percent. Although reasonably effective in its ability to mask bodily fluids, it is believed that the opacity can be improved upon to further mask the bodily fluids stored in the absorbent core. The multilayer formed-films made according to the present invention preferably have an opacity greater than about 40 percent and most preferably have an opacity greater than about 45 percent.

Exemplary, nonlimiting uses for the multilayer formed-films of this invention include topsheets for diapers, adult incontinent products, sanitary napkins and pantiliners. The multilayer formed-film topsheets can be made according to anyone of the material and filler combinations described above. One prepared combination found to work well at masking bodily fluids and providing comfort to the wearer is an approximately 0.025 mm (0.001 inches) thick multilayer film 120 having outer layers 122 of low density polyethylene and linear low density polyethylene, and a central layer 124 of low density polyethylene and linear low density polyethylene having about 40 weight percent titanium dioxide dispersed therein. Another preferred composition for topsheet applications has been found to be constructed from a film with a 3/1 ratio of LDPE/LLPDE. The center layer of the film can contain from 40% to 60% titanium dioxide without importantly altering the physical properties of the film. The outer layers 122 comprise approximately four-tenths of the total multilayer film 120 thickness and the central filler containing opacifying layer 124 comprises about six-tenths of the total multilayer film 120 thickness.

In use an absorbent bandage is placed on the undergarment of the wearer with the formed-film multilayer topsheet facing the skin. Vaginal discharge or menses will be deposited on the formed-film topsheet, and drain through the topsheet to the absorbent core where such discharge or menses will be masked by the opaque multilayer formed-film of the present invention. The discharge or menses will be retained in the core by the unapertured backsheet.

It is recognized that various modifications to the invention can be made and various combinations of polymers and fillers, including those discussed above and others, can be utilized without departure from the spirit and scope of the present invention. Accordingly, the present invention comprises all embodiments within the scope of the appended claims.

What is claimed is:

1. At substantially polymeric multilayer film which exhibits an opaque appearance, said polymeric multilayer film comprising:
    (a) a first outer layer comprised substantially of a polymer;
    (b) a central filler-containing polymeric layer having a first side and a second side opposed thereto, said first side being substantially continuously joined to one side of said first outer layer, said filler-containing polymeric layer having about 20 to about 60 weight percent fillers relative to said filler-containing layer and being substantially uniformly dispersed therein, and a thickness from about 30 to about 70 percent of the total thickness of said multilayer film; and
    (c) a second outer layer comprised substantially of a polymer and having one side substantially continuously joined to said second side of said central filler-containing layer, said multilayer film having at least 20 weight percent fillers relative to said total multilayer film such that said fillers in said central filler-containing layer scatter light rays incident upon said multilayer film to produce said opaque appearance in said multilayer film.

2. A multilayer film according to claim 1, wherein said filler-containing layer comprises fillers selected from the group consisting of titanium dioxide, calcium carbonate, silica, colored pigments, filaments and combinations thereof.

3. A multilayer film according to claim 1, wherein said filler-containing layer comprises polymers selected from the group consisting of polyolefins, copolymers having at least one olefinic constituent, polyesters, nylons, copolymers of polyesters and nylons, and combinations thereof.

4. A multilayer film according to claim 3, wherein said filler-containing layer comprises polymers selected from the group consisting of polyethylenes, polypropylenes, ethylene vinyl acetate copolymer and combinations thereof.

5. A multilayer film according to claim 1, wherein said outer layers comprise polymers selected from the group consisting of polyolefins, copolymers having at least one olefinic constituent, polyesters, nylons, copolymers of polyesters and nylons and combinations thereof.

6. A multilayer film according to claim 5, wherein said outer layers comprise polymers selected from the group consisting of polyethylenes, polypropylenes and combinations thereof.

7. A multilayer film according to claim 5, further comprising from about 1 to about 15 weight percent fillers dispersed in said outer layers.

8. A multilayer film according to claim 1, wherein said outer layers comprise substantially different compositions from each other.

9. A substantially polymeric multilayer formed-film having a multiplicity of apertures therein which exhibits an opaque appearance, said polymeric multilayer formed-film comprising:
(a) a first outer layer comprised substantially of a polymer;
(b) a central filler-containing polymeric layer having a first side and a second side opposed thereto, said first side being substantially continuously joined to one side of said first outer layer, said filler-containing polymeric layer having about 20 to about 60 weight percent fillers relative to said filler-containing layer and being substantially uniformly dispersed therein, and a thickness from about 30 to about 70 percent of the total thickness of said multilayer formed-film;
(c) a second outer layer comprised substantially of a polymer and having one side substantially continuously joined to said second side of said central filler-containing layer, said multilayer formed-film having at least 20 weight percent fillers relative to said total multilayer formed-film such that said fillers in said central filler-containing layer scatter light rays incident upon said multilayer formed-film to produce said opaque appearance in said multilayer formed-film;
and said multilayer formed-film having a multiplicity of apertures therein.

10. A multilayer formed-film according to claim 9, wherein said filler-containing layer comprises fillers selected from the group consisting of titanium dioxide, calcium carbonate, silica, colored pigments, filaments and combinations thereof.

11. A multilayer formed-film according to claim 9, wherein said filler-containing layer comprises polymers selected from the group consisting of polyolefins, copolymers having at least one olefinic constituent, polyesters, nylons, copolymers of polyesters and nylons, and combinations thereof.

12. A multilayer formed-film according to claim 9, wherein said fillercontaining layer comprises polymers selected from the group consisting of polyethylenes, polypropylenes, ethylene vinyl acetate copolymer and combinations thereof.

13. A multilayer formed-film according to claim 9, wherein said outer layers comprise polymers selected from the group consisting of polyolefins, copolymers having at least one olefinic constituent, polyesters, nylons, copolymers of polyesters and nylons and combinations thereof.

14. A multilayer formed-film according to claim 13, wherein said outer layers comprise polymers selected from the group consisting of polyethylenes, polypropylenes and combinations thereof.

15. A multilayer formed-film according to claim 13, further comprising from about 1 to about 15 weight percent fillers dispersed in said outer layers.

16. A multilayer formed-film according to claim 9, wherein said outer layers comprise substantially different compositions from each other.

17. An absorbent bandage including a substantially polymeric multilayer formed-film topsheet having a multiplicity of apertures therein, a backsheet resistant to the passage of aqueous fluid therethrough and an absorbent element for absorbing bodily fluids positioned between said topsheet and said backsheet, said polymeric multilayer formed-film topsheet comprising:
(a) a first outer layer comprised substantially of a polymer;
(b) a central filler-containing polymeric layer having a first side and a second side opposed thereto, said first side being substantially continuously joined to one side of said first outer layer, said filler-containing polymeric layer having about 20 to about 60 weight percent fillers relative to said filler-containing layer and being substantially uniformly dispersed therein, and a thickness from about 30 to about 70 percent of the total thickness of said multilayer formed-film; and
(c) a second outer layer comprised substantially of a polymer and having one side substantially continuously joined to said second side of said central filler-containing layer, said multilayer formed-film having at least 20 weight percent fillers relative to said total thickness of said multilayer formed-film such that said fillers in said central filler-containing layer scatter light rays incident upon said multilayer formed-film to produce said opaque appearance in said multilayer formed-film.

18. The structure of claim 17, wherein said absorbent bandage comprises a catamenial appliance.

* * * * *